(12) United States Patent
Videen

(10) Patent No.: US 6,239,873 B1
(45) Date of Patent: May 29, 2001

(54) APPARATUS FOR SIMULTANEOUS MEASUREMENT OF TWO POLARIZATION STATES OF SCATTERED LIGHT

(75) Inventor: Gorden Videen, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/710,747

(22) Filed: Nov. 13, 2000

(51) Int. Cl.[7] .................................................. G01B 11/06
(52) U.S. Cl. .............................................................. 356/369
(58) Field of Search .................................... 356/369, 382, 356/381, 367, 364

(56) References Cited

U.S. PATENT DOCUMENTS

| | | | |
|---|---|---|---|
| 4,730,293 | * | 3/1988 | Pierce et al. ............................. 369/44 |
| 4,850,711 | * | 7/1989 | Sano et al. ............................. 356/382 |
| 5,166,752 | * | 11/1992 | Spanier et al. ........................ 356/369 |
| 5,420,680 | * | 5/1995 | Isobe et al. ............................ 356/128 |
| 5,477,327 | * | 12/1995 | Bergman .............................. 356/367 |
| 6,069,690 | * | 5/2000 | Xu et al. ................................. 356/73 |
| 6,079,256 | * | 6/2000 | Bareket ................................. 73/105 |

* cited by examiner

Primary Examiner—Robert H. Kim
Assistant Examiner—Michael P. Stafira
(74) Attorney, Agent, or Firm—Paul S. Clohan, Jr.

(57) ABSTRACT

A device for simultaneous measurement of two polarization states of scattered light includes an illumination unit having first and second lasers for providing first and second beams of polarized light $\lambda_1$ and $\lambda_2$, which have different wavelengths and different polarization states. A first beamsplitter is positioned for receiving the first and second polarized beams. After exiting the first beamsplitter, the light beams are coincident with each other and pass through an aperture to illuminate a sample. A measuring unit includes a second polarization beamsplitter for receiving at least a portion of each of the first and second light beams after illuminating the sample. Notch filters are positioned for receiving the portions of the first and second light beams which have exited the second beamsplitter, so that a first notch filter filters all of the first light beam except for a range of wavelengths which includes the first wavelength, and does not include the second wavelength, while a second notch filter filters all of the second light beam except for a range of wavelengths which includes the second wavelength of the second beam, and does not include the first wavelength of the first beam.

20 Claims, 2 Drawing Sheets

APPARATUS FOR SIMULTANEOUS MEASUREMENT OF TWO POLARIZATION STATES OF SCATTERED LIGHT

BACKGROUND OF THE INVENTION

1. Field of the Invention

The present invention relates generally to a device for measurement of polarized light. More specifically, the present invention relates to devices for simultaneous measurement of two orthogonal polarization states of scattered light.

2. Description of the Related Art

Scattering systems normally project polarized light from a single source toward a sample and measure at least a portion of the light which scatters off the sample at different scattering angles to provide information about the sample.

The simultaneous measurement of two orthogonal polarization states of scattered light from a sample is often desired to compare the intensities of the two polarized states as a means to identify characteristics of the sample. However, to accomplish this, a complicated system is required, which includes a series of modulators, such as electro-optic crystals, and control means to operate the modulators.

SUMMARY OF THE INVENTION

Accordingly, it is an object of the present invention to overcome the problems of the prior art.

To this end, according to the present invention, there is provided an apparatus for simultaneous measurement of two polarization states of scattered light, the apparatus comprising:

(a) an illumination unit comprising:
    a first laser unit for providing a first beam of polarized light having a first wavelength $\lambda_1$ and a first state of polarization;
    a second laser unit for providing a second beam of polarized light having a second wavelength $\lambda_2$, which is different from the first wavelength, and a second state of polarization; which is different from the first state of polarization;
    a first polarization beamsplitter positioned for receiving the first and second light beams, so that the first and second light beams are coincident with each other after exiting the first beamsplitter, the first beamsplitter for passing the first light beam and reflecting the second light beam;
    an aperture unit for providing a passage of the first and second light beams after exiting the first beamsplitter to illuminate a sample; and (b) a measuring unit comprising:
    a second polarization beamsplitter positioned for receiving at least a portion of the first light beam and a portion of the second light beam after illuminating the sample, the second beamsplitter for passing the portion of the first light beam and reflecting the portion of the second light beam;
    a first notch filter positioned for receiving the portion of the first light beam which has exited the second beamsplitter, the first notch filter for filtering the portion of the first light beam except for a range of wavelengths which includes the first wavelength of the first beam and which does not include the second wavelength of the second beam; and
    a second notch filter positioned for receiving the portion of the second light beam which has been reflected by the second beamsplitter, the second notch filter for filtering the portion of the second light beam except for a range of wavelengths which includes the second wavelength of the second beam and which does not include the first wavelength of the first beam.

The illumination may further include a first spatial filter unit for collimating the first beam provided by the first laser unit, the first spatial filter unit being positioned in an optical path between the first laser unit and the first beamsplitter; and a second spatial filter unit for collimating the second beam provided by the second laser unit, the second spatial filter unit being positioned in an optical path between the second laser unit and the first beamsplitter.

The measuring unit may further include:
    a third spatial filter unit for collimating the portion of the first beam and the portion of the second beam after illuminating the sample, the third spatial filter unit being positioned in an optical path between the sample and the second beamsplitter.

According to an aspect of the invention, a length of both of the first wavelength $\lambda_1$ and the second wavelength $\lambda_2$ may satisfy the following equation:

$$|\lambda_1 - \lambda_2| \ll \lambda_1.$$

In addition, the first laser unit and the second laser unit comprise diode lasers.

The first laser unit and the second laser unit may comprise diode lasers.

The first state of polarization of the first beam of light is s-polarization, and the second state of polarization of the second beam of light is p-polarization.

In addition, the first notch filter and the second notch filter provide a respective output of light to a measuring unit for measuring an intensity of the respective outputs.

According to another embodiment of the present invention, an apparatus for simultaneous measurement of two polarization states of scattered light, the apparatus comprising:

(a) an illumination unit comprising:
    a first laser unit for providing a first beam of polarized light having a first wavelength $\lambda_1$ and a first state of polarization;
    a second laser unit for providing a second beam of polarized light having a second wavelength $\lambda_2$, which is different from the first wavelength, and a second state of polarization, which is different from the first state of polarization;
    a first polarization-preserving beamsplitter positioned to receive the first and second light beams so that the first and second light beams are coincident with each other after exiting the first beamsplitter, the first beamsplitter for passing the first light beam and reflecting the second light beam;
    an aperture unit for providing a passage of the first and second light beams after exiting the first beamsplitter to illuminate a sample; and (b) a measuring unit comprising:
    a second polarization-preserving beamsplitter positioned for receiving at least a portion of the first light beam and a portion of the second light beam after illuminating the sample, the second beamsplitter for passing the portion of the first light beam and reflecting the portion of the second light beam;
    a first notch filter positioned for receiving the portion of the first light beam having the first polarized state, which has been passed by the second beamsplitter, the first notch filter for filtering the portion of the first light beam except for a range of wavelengths which includes the first wavelength of the first beam and which does not include the second wavelength of the second beam; and a second notch filter positioned for receiving the portion of the second light beam having the second polarized state, which has been reflected by the second beamsplitter, the second notch filter for filtering the portion of the second light beam except for a range of wavelengths which includes the second wavelength of the second beam and which does not include the first wavelength of the first beam.

The illumination unit may further include:

a first spatial filter unit for collimating the first beam provided by the first laser unit, the first spatial filter unit being positioned in an optical path between the first laser unit and the first beamsplitter;

a second spatial filter unit for collimating the second beam provided by the second laser unit, the second spatial filter unit being positioned in an optical path between the second laser unit and the first beamsplitter;

a first polarizer positioned between the first spatial filter unit and the first beamsplitter; and a second polarizer positioned between the second spatial filter unit and the first beamsplitter.

The measuring unit may further include:

a third spatial filter unit for collimating the portion of the first beam and the portion of the second beam after illuminating the sample, the third spatial filter unit being positioned in an optical path between the sample and the second beamsplitter;

a third polarizer positioned between the first notch filter and the second polarization-preserving beamsplitter; and a fourth polarizer positioned between the second notch filter and the second polarization-preserving beamsplitter.

In addition, the apparatus may include a rotation unit for rotating at least one of the first, second, third and fourth polarizers.

According to this embodiment, a length of both of the first wavelength $\lambda_1$ and the second wavelength $\lambda_2$ may satisfy the following equation:

$$|\lambda_1-\lambda_2|<<\lambda_1.$$

In addition, the first state of polarization of the first beam of light may be s-polarization and the second state of polarization of the second beam of light may be p-polarization.

The apparatus may include a unit for moving the illumination unit and the measuring unit relative to the sample.

DETAILED DESCRIPTION OF THE PREFERRED EMBODIMENTS

In the embodiments described below, the two orthogonal states of polarized light which are simultaneously measured comprise p-polarized and s-polarized light. P-polarized light comprises an electric field in the plane of incidence containing the incident beam and reflected beam, and s-polarized light comprises an electric field perpendicular to the plane of incidence.

Accordingly, it is understood by a person of ordinary skill in the art that an electric field of a polarized light wave is perpendicular to a vector (typically referred to as K), which represents the incident light propagation direction.

It will also be understood by a person of ordinary skill in the art that the present invention is not limited to measurements of p-polarized and s-polarized light.

Figure 1:
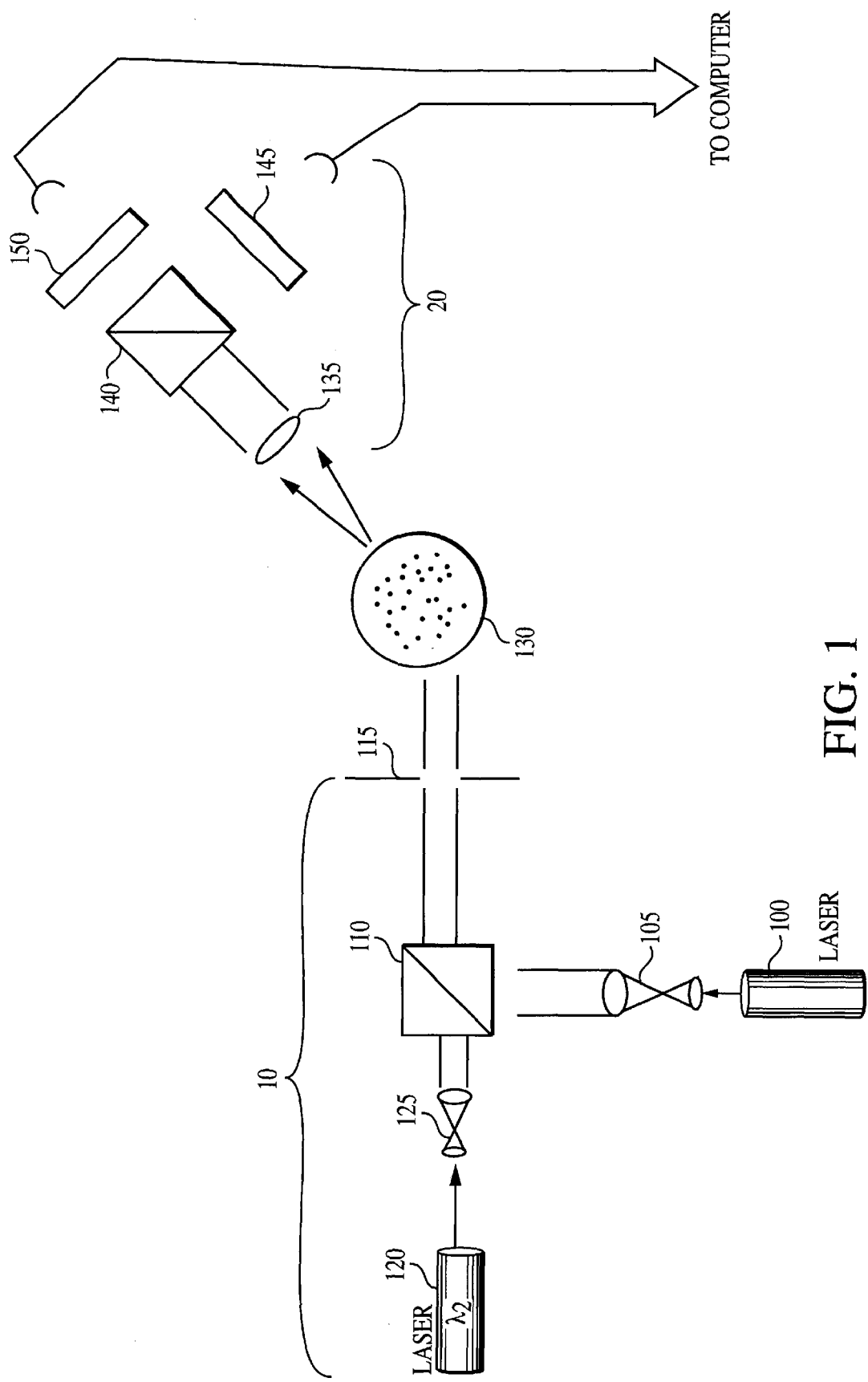
FIG. 1 illustrates a first embodiment of a device for simultaneous measurement of two orthogonal polarization states according to the present invention.

FIG. 1 illustrates a first embodiment of the simultaneous measurement device of two orthogonal polarization states according to the present invention.

An illumination unit 10 includes the hardware for providing and adjusting two beams of light prior to striking (illuminating) a sample 130. The illumination portion comprises a first laser 100, which transmits a first light beam that has been s-polarized either within the laser or by passage through a polarizer. The s-polarized light is then collimated by a collimator, for example, a spatial filter system 105. After being collimated, the light is then reflected by polarizing beamsplitter 110 towards aperture 115.

At the same time that first laser 100 transmits the first light beam, which has been s-polarized, a second laser 120 transmits a second light beam which has been p-polarized either within the laser 120 or by passage through a polarizer. The p-polarized light is then collimated by a collimator, for example, a spatial filter 125, before passing through polarizing beamsplitter 110 towards aperture 115.

The incident beams from both the first and second lasers become coincident with each other after exiting the beamsplitter 110, and then pass through the aperture 115 to illuminate the sample 130. The light is scattered from both incident beams which illuminate the sample.

A measuring unit 20 includes the hardware for receiving and processing the light beams subsequent to their illuminating the sample.

At least a portion of the light which strikes the sample 130 is reflected through a collimating lens 135 before entering a polarizing beamsplitter 140, which passes p-polarized light and reflects s-polarized light.

The s-polarized light, which is reflected by polarizing beam splitter 140, subsequently strikes first notch filter 145. The first notch filter 145 allows passage of a small range of wavelengths of light near the wavelength of the first laser 100, and this range does not include the wavelength of the second laser 120. The intensity of the light which exits the first notch filter 145 is measured by, for example, a photodetector and recorded, for example, as signal LSS.

The p-polarized light that is transmitted through the beamsplitter strikes a second notch filter 150. The second notch filter 150 allows light to pass within a small range of wavelengths near the wavelength of the second laser 120, and this range does not include the wavelength of the first laser 100. The intensity of the light which exits the second notch filter 150 is measured by, for example, a photodetector and recorded, for example, as signal LPP.

Signals LSS and LPP are analyzed by a computer (not shown).

The respective wavelengths of the first and second lasers, $\lambda_1$ and $\lambda_2$, may be similar but not equal to each other, such that:

$$|\lambda_1-\lambda_2|<<\lambda;$$

and the polarization state of $\lambda_1$ and $\lambda_2$ should be different. For example, in this embodiment, $\lambda_1$ could be 680 nm and $\lambda_2$ could be 660 nm, with $\lambda_1$ being s-polarized and $\lambda_2$ being p-polarized.

Figure 2:
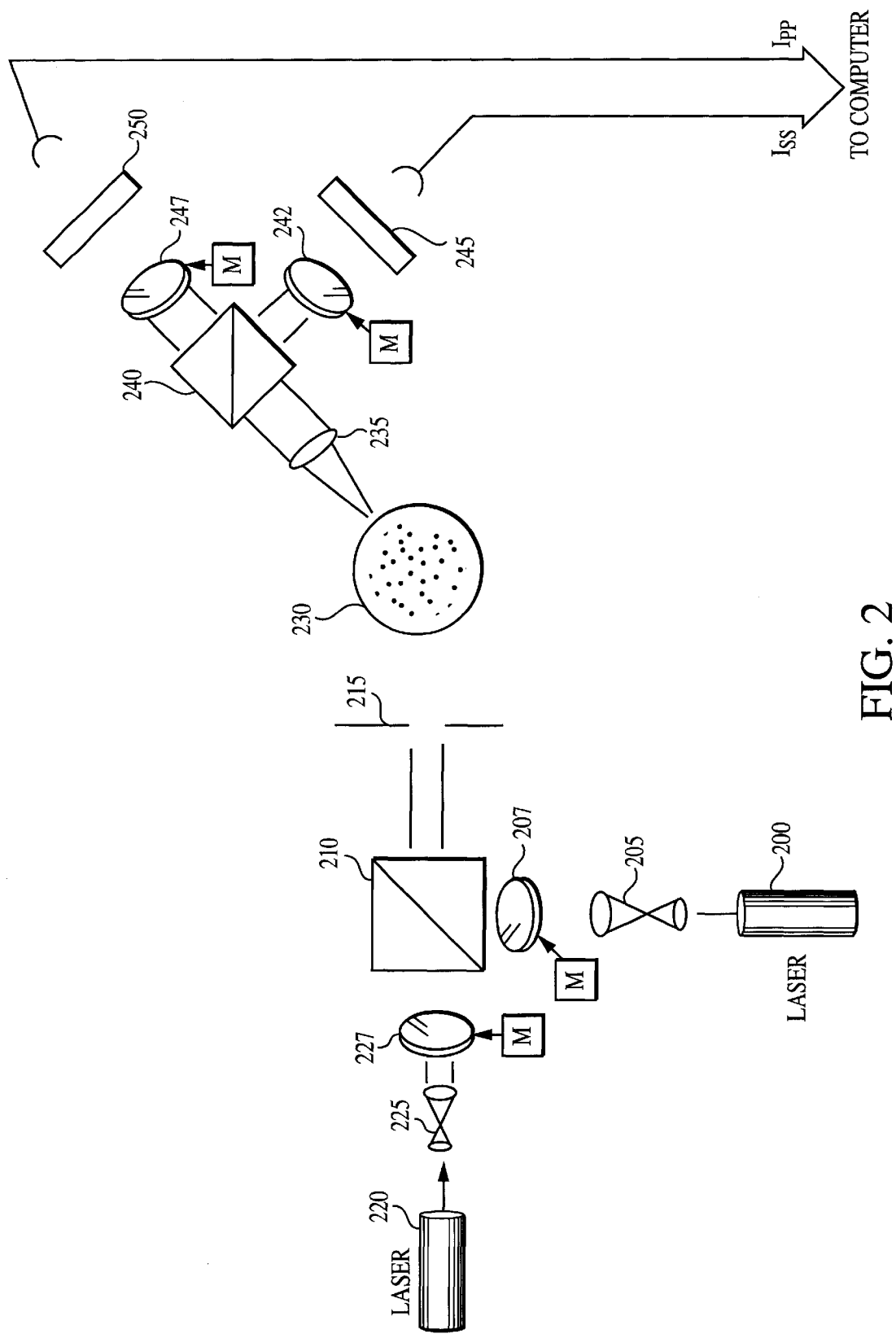
FIG. 2 illustrates a second embodiment of a device for simultaneous measurement of two orthogonal polarization states according to the present invention.

FIG. 2 illustrates a second embodiment according to the present invention.

Similar to the first embodiment, a first laser 200 transmits s-polarized light, which may be polarized within the laser or by passing through a polarizer, and the s-polarized light is then collimated by a collimator, for example, a spatial filter system 205. At the same time that first laser 200 transmits s-polarized light, a second laser 220 transmits p-polarized light, which also may be polarized within the laser or by passing through a polarizer, and is collimated by a collimator, for example, a spatial filter 225.

However, as shown in FIG. 2, the collimated light from the first and second lasers each pass through respective polarizers 207, 227 before becoming coincident with each other after striking a polarization-preserving beamsplitter 210. After passing through aperture 215, the coincident beams illuminate the sample 230 and are scattered.

At least a portion of the light which is scattered after striking the sample 230 is collimated by a collimating lens 235 before striking polarization-preserving beamsplitter 240.

The s-polarized light, which is reflected by polarizing beam splitter 240, subsequently passes through polarizer 242 before striking a first notch filter 245. The first notch filter 245 allows passage of a small range of wavelengths of light near the wavelength of the first laser 200, which does not include the wavelength of the second laser 220. The intensity of the light which leaves the first notch filter is measured by, for example, a photodetector, and recorded, for example, as signal LSS.

In addition, the p-polarized light that is transmitted through the beamsplitter 240 passes through polarizer 247 before striking a second notch filter 250. The second notch filter 250 allows light to pass within a small range of wavelengths near the wavelength of the second laser 220, which does not include the wavelength of the first laser 200. The intensity of the light which leaves the second notch filter is measured by, for example, a photodetector and recorded, for example, as signal LPP. A computer (not shown) analyzes signals LSS and LPP.

In this embodiment, the respective wavelengths of the first and second lasers, $\lambda_1$ and $\lambda_2$, may also be similar but unequal to each other, such that:

$$|\lambda_1 - \lambda_2| << \lambda_1;$$

and the polarization state of $\lambda_1$ and $\lambda_2$ should be different.

Some or all of the polarizers 207, 227, 242 and 247 may be rotatable by a rotation unit 248. The rotation of the polarizers may provide additional information about the particle symmetry of the sample 230 by the detected difference in the intensity of scattered light detected from the different positions of the rotated polarizers.

The entire device may be either mounted on an arm (not shown), which can move relative to the sample, to move around the sample and measure the polarization states of the scattered light as a function of the scattering angle.

Various modifications and adaptations may be made to the disclosed embodiments by those skilled in the art, which fall within the scope and spirit of the appended claims.

For example, the wavelengths of the two lasers may be chosen for detection of a specific type of sample. The lasers may be diode lasers, and the specific type of polarizers can vary according to need.

What is claimed is:

1. An apparatus for simultaneous measurement of two polarization states of scattered light, said apparatus comprising:
    (a) an illumination unit comprising:
        a first laser means for providing a first beam of polarized light having a first wavelength $\lambda_1$ and a first state of polarization;
        a second laser means for providing a second beam of polarized light having a second wavelength $\lambda_2$, which is different from said first wavelength, and a second state of polarization, which is different from said first state of polarization;
        a first polarization beamsplitter positioned for receiving the first and second light beams, so that the first and second light beams are coincident with each other after exiting said first beamsplitter, said first beamsplitter for passing the first light beam and reflecting the second light beam;
        an aperture means for providing a passage of the first and second light beams after exiting said first beamsplitter to illuminate a sample; and
    (b) a measuring unit comprising:
        a second polarization beamsplitter positioned for receiving at least a portion of the first light beam and a portion of the second light beam after illuminating the sample, said second beamsplitter for passing the portion of the first light beam and reflecting the portion of the second light beam;
        a first notch filter positioned for receiving the portion of the first light beam which has exited said second beamsplitter, said first notch filter for filtering the portion of the first light beam except for a range of wavelengths which includes said first wavelength of said first beam and which does not include said second wavelength of said second beam; and
        a second notch filter positioned for receiving the portion of the second light beam which has been reflected by said second beamsplitter, said second notch filter for filtering the portion of the second light beam except for a range of wavelengths which includes said second wavelength of said second beam and which does not include said first wavelength of said first beam.

2. The device according to claim 1, wherein said illumination unit further comprises:
    a first spatial filter means for collimating the first beam provided by said first laser means, said first spatial filter means being positioned in an optical path between said first laser means and said first beamsplitter; and
    a second spatial filter means for collimating the second beam provided by said second laser means, said second spatial filter means being positioned in an optical path between said second laser means and said first beamsplitter.

3. The device according to claim 2, wherein said measuring unit further comprises:
    a third spatial filter means for collimating said portion of the first beam and said portion of said, second beam after illuminating the sample, said third spatial filter means being positioned in an optical path between the sample and said second beamsplitter.

4. The device according to claim 1, wherein a length of both of said first wavelength $\lambda_1$ and said second wavelength $\lambda_2$ satisfy the following equation:

$$|\lambda_1 - \lambda_2| << \lambda_1.$$

5. The device according to claim 3, wherein a length of both of said first wavelength $\lambda_1$ and said second wavelength $\lambda_2$ satisfy the following equation:

$$|\lambda_1-\lambda_2|<<\lambda_1.$$

6. The device according to claim 1, wherein said first laser means and said second laser means comprise diode lasers.

7. The device according to claim 5, wherein said first laser means and said second laser means comprise diode lasers.

8. The device according to claim 1, wherein said first state of polarization of said first beam of light is s-polarization.

9. The device according to claim 8, wherein said second state of polarization of said second beam of light is p-polarization.

10. The device according to claim 1, wherein said first notch filter and said second notch filter provide a respective output of light to a measuring means for measuring an intensity of the respective outputs.

11. An apparatus for simultaneous measurement of two polarization states of scattered light, said apparatus comprising:
  (a) an illumination unit comprising:
    a first laser means for providing a first beam of polarized light having a first wavelength $\lambda_1$ and a first state of polarization;
    a second laser means for providing a second beam of polarized light having a second wavelength $\lambda_2$, which is different from said first wavelength, and a second state of polarization, which is different from said first state of polarization;
    a first polarization-preserving beamsplitter positioned to receive the first and second light beams so that the first and second light beams are coincident with each other after exiting said first beamsplitter, said first beamsplitter for passing the first light beam and reflecting the second light beam;
    an aperture means for providing a passage of the first and second light beams after exiting said first beamsplitter to illuminate a sample; and
  (b) a measuring unit comprising:
    a second polarization-preserving beamsplitter positioned for receiving at least a portion of the first light beam and a portion of the second light beam after illuminating the sample, said second beamsplitter for passing the portion of the first light beam and reflecting the portion of the second light beam;
    a first notch filter positioned for receiving the portion of the first light beam having the first polarized state, which has been passed by said second beamsplitter, said first notch filter for filtering the portion of the first light beam except for a range of wavelengths which includes said first wavelength of said first beam and which does not include said second wavelength of said second beam; and
    a second notch filter positioned for receiving the portion of the second light beam having the second polarized state, which has been reflected by said second beamsplitter, said second notch filter for filtering the portion of the second light beam except for a range of wavelengths which includes said second wavelength of said second beam and which does not include said first wavelength of said first beam.

12. The device according to claim 11, wherein said illumination unit further comprises:
  a first spatial filter means for collimating the first beam provided by said first laser means, said first spatial filter, means being positioned in an optical path between said first laser means and said first beamsplitter;
  a second spatial filter means for collimating the second beam provided by said second laser means, said second spatial filter means being positioned in an optical path between said second laser means and said first beamsplitter;
  a first polarizer positioned between said first spatial filter means and said first beamsplitter; and
  a second polarizer positioned between said second spatial filter means and said first beamsplitter.

13. The device according to claim 12, wherein said measuring unit further comprises:
  a third spatial filter means for collimating said portion of the first beam and said portion of the second beam after illuminating the sample, said third spatial filter means being positioned in an optical path between the sample and said second beamsplitter;
  a third polarizer positioned between said first notch filter and said second polarization-preserving beamsplitter; and
  a fourth polarizer positioned between said second notch filter and said second polarization-preserving beamsplitter.

14. The device according to claim 13, further comprising means for rotating at least one of the first, second, third and fourth polarizers.

15. The device according to claim 11, wherein a length of both of said first wavelength $\lambda_1$ and said second wavelength $\lambda_2$ satisfy the following equation:

$$|\lambda_1-\lambda_2|<<\lambda_1.$$

16. The device according to claim 14, wherein a length of both of said first wavelength $\lambda_1$ and said second wavelength $\lambda_2$ satisfy the following equation:

$$|\lambda_1-\lambda_2|<<\lambda_1.$$

17. The device according to claim 11, wherein said first state of polarization of said first beam of light is s-polarization.

18. The device according to claim 17, wherein said second state of polarization of said second beam of light is p-polarization.

19. The device according to claim 1, further comprising means for moving said illumination unit and said measuring unit relative to the sample.

20. The device according to claim 11, further comprising means for moving said illumination unit and said measuring unit relative to the sample.

* * * * *